(12) United States Patent
Kawaguchi et al.

(10) Patent No.: US 7,854,918 B2
(45) Date of Patent: Dec. 21, 2010

(54) COMPOSITION FOR MEDICAL USE HAVING IMPROVED WATER-SOLUBILITY OF PEPTIDE AND METAL-LABELING EFFICIENCY AND PREPARATION FOR MEDICAL USE COMPRISING METAL-LABELED PEPTIDE

(75) Inventors: Takayoshi Kawaguchi, Sodegaura (JP); Ikuya Seki, Sodegaura (JP); Marino Maemura, Sodegaura (JP)

(73) Assignee: Nihon Medi-Physics Co., Ltd., Tokyo (JP)

( * ) Notice: Subject to any disclaimer, the term of this patent is extended or adjusted under 35 U.S.C. 154(b) by 1136 days.

(21) Appl. No.: 10/591,252

(22) PCT Filed: Mar. 23, 2005

(86) PCT No.: PCT/JP2005/005182

§ 371 (c)(1),
(2), (4) Date: Aug. 31, 2006

(87) PCT Pub. No.: WO2005/092396

PCT Pub. Date: Oct. 6, 2005

(65) Prior Publication Data

US 2007/0160532 A1 Jul. 12, 2007

(30) Foreign Application Priority Data

Mar. 25, 2004 (JP) .............................. 2004-089620

(51) Int. Cl.
*A61K 51/00* (2006.01)
*A61M 36/14* (2006.01)

(52) U.S. Cl. .............. 424/1.69; 424/1.11; 424/1.65; 530/300; 530/327; 530/328; 530/329

(58) Field of Classification Search .............. 424/1.11, 424/1.49, 1.65, 1.69, 1.81, 1.85, 1.89, 9.1, 424/9.3, 9.4, 9.5, 9.6, 9.7, 9.8; 530/300, 530/327, 328, 329, 331, 333, 338
See application file for complete search history.

(56) References Cited

U.S. PATENT DOCUMENTS 5,891,418 A 4/1999 Sharma
7,220,827 B2 * 5/2007 Seki et al. .................. 530/328

FOREIGN PATENT DOCUMENTS

WO 95/11045 A1 4/1995

OTHER PUBLICATIONS

Behr, T.M. et al., Reduction of the renal uptake of radiolabeled monoclonal antibody fragments by cationic amino acids and their derivatives, Cancer research, 1995, vol. 55, No. 17, p. 3825-34.
Verbeke, K. et al., Influence of the bifunctional chelate on the biological behavior of (99m)Tc-labeled chemotactic peptide conjugates, Nucl. Med. Biol., 2000, vol. 27, No. 8, p. 769-79.
Van Der Laken, C. J. et al., Technetium-99m-labeled Chemotactic Peptides in acute infection and sterile inflammation; The Journal of Nuclear Medicine, vol. 38, No. 8, Aug. 1997, p. 1310-1315.

* cited by examiner

*Primary Examiner*—D L Jones
(74) *Attorney, Agent, or Firm*—Sughrue Mion, PLLC

(57) ABSTRACT

By preliminarily dissolving a basic organic compound in an aqueous solvent in which a peptide usable in metal-labeling is to be dissolved, the solubility of the peptide is improved and thus metal-labeling can be carried out without heating. A composition for medical use containing a peptide usable in metal-labeling and a basic organic compound acceptable as a pharmaceutical additive can be utilized as a preparation useful in image diagnosis, radiotherapy and so on.

17 Claims, 4 Drawing Sheets

ELUTION RATES OF PEPTIDE 1, PEPTIDE 2, AND PEPTIDE 3

COMPARISON OF ELUTION RATES OF PEPTIDE 1 BY ADDITION OF A VARIETY OF ADDITIVES AT pH 9

COMPOSITION FOR MEDICAL USE HAVING IMPROVED WATER-SOLUBILITY OF PEPTIDE AND METAL-LABELING EFFICIENCY AND PREPARATION FOR MEDICAL USE COMPRISING METAL-LABELED PEPTIDE

TECHNICAL FIELD

The present invention relates to a medical composition having improved water-solubility and metal-labeling efficiency of a peptide capable of being labeled with a metal, which comprises a peptide capable of being labeled with a metal, to a medical preparation comprising the above-described peptide that is labeled with a metal, and to a method for labeling the above-described peptide with a metal. To be more specific, the present invention relates to a medical composition obtained by dissolving a peptide capable of being labeled with a metal, which is insoluble or poorly soluble in an aqueous solvent, together with a basic organic compound in the aqueous solvent, wherein the metal-labeling efficiency of the above-described peptide at room temperature improves; to a medical preparation obtained by labeling, with a metal, the above-described peptide in the above-described medical composition; and to a method for labeling the above-described peptide with a metal.

BACKGROUND ART

A peptide having a group, in the molecule, which is capable of being labeled with a metal can be used as an active ingredient in diagnostic or therapeutic agents by labeling the peptide with a radioactive metal, a paramagnetic metal, or the like.

The solubility of a peptide capable of being labeled with a metal decreases in an aqueous solvent with the increase in the number of hydrophobic moieties such as an alkyl group in the peptide structure. A conventional approach to dissolve such a peptide in the aqueous solvent is as follows: the peptide is dissolved in advance in an organic solvent such as dimethylsulfoxide (DMSO), dimethylformamide (DMF); and then the resulting solution is mixed with a required amount of water or a buffer solution or an aqueous solution of a certain substance. For example, formyl-Met-Leu-Phe (FMLP), one of peptides, is known to be poorly soluble in a neutral buffer solution. To dissolve the compound formyl-Met-Leu-Phe-Lys-hydrazinonicotinamide (fMLFK-HYNIC), which is a derivative of the compound FMLP to make it possible to be labeled with a metal, in an aqueous solvent, fMLFK-HYNIC is required to be dissolved with DMSO, followed by adding a necessary buffer solution or aqueous solvent (see Non-Patent Document 1).

However, in the dissolution by the above-described method, upon mixing with the aqueous solvent, the proportion of the organic solvent, which is capable of dissolving the compound, decreases in the solution. When the organic solvent falls short of a certain concentration, sometimes the peptide may become insoluble such as white turbidity and deposition.

As described above, the peptide capable of being labeled with a metal can be used as a nuclear medicine preparation by labeling it with a radioactive metal. Previous applications of dissolution of the above-described peptide with an organic solvent such as DMSO have required reaction conditions of heating at 100° C. for more than 10 minutes or reaction conditions at room temperature for more than 30 minutes for the labeling.

For example, the labeling of the fMLFK-HYNIC requires reaction conditions at room temperature for a period of 30 to 60 minutes (see Non-Patent Document 1).

Peptide derivatives of FMLP are said to be useful in the imaging of disease with leukocyte infiltration such as inflammation, while conditions under which they are capable of being labeled with a metal at room temperature in a completely aqueous solvent are unknown (see Non-Patent Document 2).

Non-Patent Document 1: van der Laken, C J. et al., J. Nucl. Med., 38, 8, 1310-1315 (1997)

Non-Patent Document 2: Verbeke, K. et al., Nuclear Medicine & Biology, Vol. 27, 769-779 (2000)

DISCLOSURE OF THE INVENTION

Problems to be Solved by the Invention

In view of the above-described problems, an object of the present invention is to provide a medical composition comprising a peptide, which is capable of being labeled with a metal without heating, wherein the peptide, which is insoluble or poorly soluble in water, becomes easy to dissolve in an aqueous solvent; a medical preparation comprising the above-described peptide that is labeled with a metal; and a metal-labeling method for the above-described peptide.

Measure for Solving the Problem

The present inventors have conducted diligent studies for attaining the object and have consequently completed the present invention by finding that, to our surprise in terms of previous findings, the above-described peptide can be prepared easily into an aqueous solution at room temperature without the use of organic solvents and surfactants and becomes capable of being labeled with a metal in a nonheated manner, by adding the peptide to a basic organic compound.

Specifically, the present invention relates to a medical composition comprising a peptide capable of being labeled with a metal and a basic organic compound acceptable as a pharmaceutical additive.

The present invention further relates to a freeze-dried medical composition characterized in that the composition is obtained by freeze-drying the above-described medical composition.

The present invention further relates to a medical preparation characterized in that the preparation is obtained by labeling, with a metal, a peptide capable of being labeled with a metal in the above-described medical composition.

The present invention further relates to a method for labeling, with a metal, a peptide capable of being labeled with a metal, characterized by comprising dissolving the above-described peptide in an aqueous solvent of a basic organic compound and then labeling the resulting product with a metal.

The present invention further relates to a method for producing a medical preparation comprising a metal-labeled peptide, characterized by using the above-described metal-labeling method.

EFFECT OF THE INVENTION

The use of the medical composition according to the present invention has improved the solubility of a peptide capable of being labeled with a metal, which is insoluble or poorly soluble in an aqueous solvent and allowed for the metal-labeling of the above-described peptide without heating. The use of the metal-labeling method according to the present invention has allowed for the labeling of the above-described peptide with a metal under nonheated conditions. Furthermore, the preparation obtained by labeling, with a metal, the above-described peptide in the medical composition according to the present invention had the advantage of improving the accumulation rate of the peptide to inflammation as compared with that of a composition prepared by a conventional method, for example when the peptide that can be used in the imaging of inflammation has been used therein. For example when a leukocyte-binding compound has been used as the peptide, the present invention has been capable of providing a medical composition and a medical preparation and a labeling method thereof being useful in PET diagnostic imaging, SPECT diagnostic imaging, and MRI diagnostic imaging that conduct the imaging of active leukocyte infiltration sites with the immune responses of individuals, or in radiation therapy.

BEST MODE FOR CARRYING OUT THE INVENTION

Figure 1:
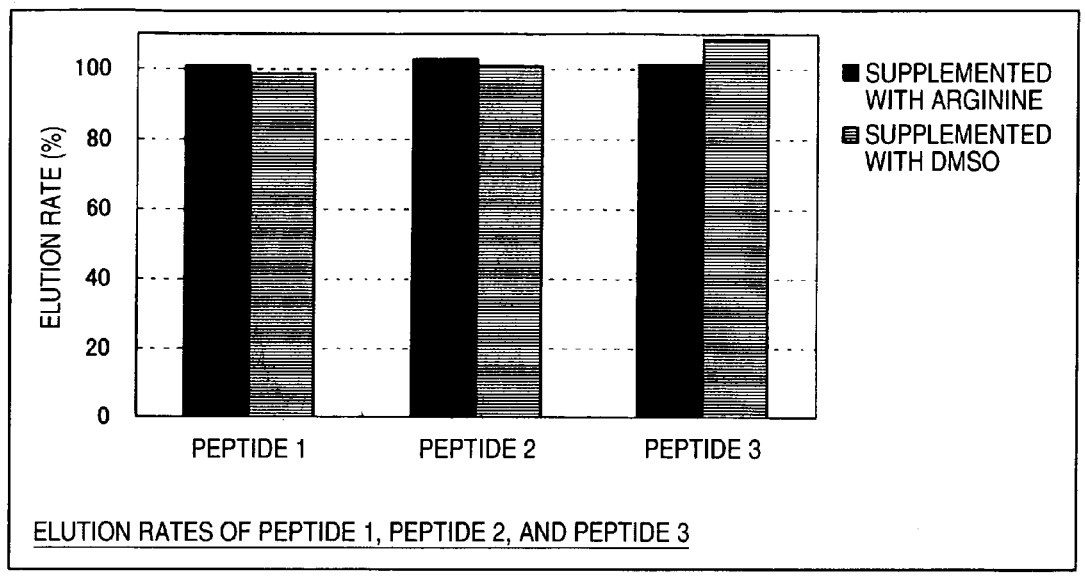
FIG. 1 is a diagram showing the elution rates of Peptide 1, Peptide 2, and Peptide 3.

Hereinafter, embodiments of the present invention will be described. All amino acids used herein are indicated by one-character or three-character codes, and the N termini and C termini thereof are indicated in the left and right, respectively, unless otherwise stated. Peptides and organic compounds bound with side chains are indicated in parentheses subsequent to amino acids, unless otherwise stated. The N termini and C termini of amino acid sequences in parentheses are indicated in the right and left, respectively, to easily understand the whole structures. In the present specification, D-form amino acids are referred to as D-amino acids.

A medical composition according to the present invention is specifically prepared by using a peptide capable of being labeled with a metal, which is insoluble or poorly soluble in an aqueous solvent, and a basic organic compound acceptable as a pharmaceutical additive as essential components to dissolve them in an aqueous solvent.

Examples of the basic organic compound include a basic amino acid and a basic compound having an imidazole ring. Examples of the basic amino acid include, but not particularly limited to, arginine, lysine, histidine, and hydroxylysine. Preferably, arginine, lysine, or histidine is used, and more preferably, arginine is used. The basic compound having an imidazole ring is not particularly limited and can be exemplified by imidazole. While one type of basic amino acid or basic compound having an imidazole ring can be used alone, two types thereof may be used in combination.

When the basic organic compound is dissolved in an aqueous solvent together with the peptide capable of being labeled with a metal, it is preferred that the basic organic compound in the medical composition should be contained in the concentration range of 0.1 mM to 1 M in the composition. The concentrations less than 0.1 mM are not preferable because labeling-promoting effect is not obtained. The concentrations higher than 1 M are not preferable because osmotic pressure and toxicity become problems. The amount of the basic organic compound used differs depending on the type of the peptide used, and so on and is usually preferably in the molarity range of 10 to 1000000 times, more preferably 1000 to 100000 times, higher than that of the peptide capable of being labeled with a metal. The molarities 10 or lower times higher than that of the peptide capable of being labeled with a metal are not preferable because sufficient dissolution-promoting effect and labeling-promoting effect by the basic organic compound are not obtained. The molarities 1000000 or higher times higher than that of the peptide capable of being labeled with a metal are not preferable because the above-described basic organic compound existing in an excess amount has inhibitory action on labeling.

In the above-described concentration range, the pH of a solution preferable as the composition ranges from 8 to 12, more preferably 8.5 to 12. The pH more acidic than 8 is not preferable because dissolution-promoting effect by the basic organic compound is impaired. The pH more alkaline than 12 is not preferable because it might adversely affect living bodies.

The peptide capable of being labeled with a metal that is used in the present invention is specifically a peptide insoluble or poorly soluble in an aqueous solvent and is preferably a peptide available as an active ingredient in a diagnostic drug or a pharmaceutical drug for therapeutic use. A polyamino acid compound having 30 or less amino acid residues or a molecular weight of 4500 or less is more preferable. The peptide may contain an amino group or carbonyl group in its structure. The above-described peptide is not particularly limited as long as it is capable of being labeled with a metal. For example, a leukocyte-binding compound can be used as the peptide when used in the diagnosis of inflammation or the like.

A compound represented by the following formula (1):

[Formula 1]

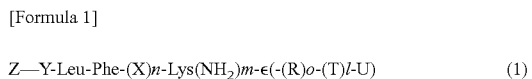

is preferably used as the peptide used in the present invention. In this context, chemical formula (1) consists of: Z-Y-Leu-Phe-, a formyl peptide receptor-binding site of a leukocyte; -(R)o- a binding portion that improves the rate of binding to monocytes and lymphocytes among all leukocytes; —U—, a structure capable of being labeled with a radioactive metal and paramagnetic metal; and $-(X)_n-$, $-Lys(NH_2)_m-$, and $-(T)l-$, spacers that combine them.

In chemical formula (1), Z represents a protecting group for an amino group; Y represents Met or Nle; in $(X)n$, X represents a spacer consisting of one or more amino acids or a compound capable of being organically synthesized, and n represents 1 or 0; in $(NH_2)m$, $NH_2$ represents an amide group serving as a protecting group for an α-carboxyl group of Lys, and m represents 1 or 0; and in $ε(-(R)o-(T)l-U)$, R represents Ser or Thr bound via amide bond with an ε-amino group of Lys, o represents 1 or 0, T represents a spacer consisting of one or more amino acids or a compound capable of being organically synthesized, l represents 1 or 0, and U represents a group capable of being labeled with a metal, wherein X and T may be identical or different.

In chemical formula (1), the group represented by U is not particularly limited as long as it is capable of being labeled with a metal. The group is preferably a ligand consisting of several amino acids. More specific examples thereof include a tripeptide capable of being labeled with a metal, dipeptide-mercapto-acylate, a nitrogen-containing cyclic compound having 8 to 20 carbon atoms, a nitrogen-containing cyclic carboxylic acid compound having 8 to 20 carbon atoms, a derivative of a nitrogen-containing cyclic carboxylic acid compound having 8 to 20 carbon atoms, and alkylene-amine-carboxylic acid having 4 to 10 carbon atoms. To be more specific, examples of the group that can be used include a group capable of being labeled with a metal, which is selected from a tripeptide capable of being labeled with a metal such as -Cys-Gly-Asp, -Cys-Asp-Asp, -Cys-Asp-Gly, -Cys-Gly-Glu, -Cys-Glu-Glu, -Cys-Glu-Gly, -Cys-Gly-Asn, -Cys-Asn-Asn, -Cys-Asn-Gly, -Cys-Gly-Gln, -Cys-Gln-Gln, -Cys-Gln-Gly, -Cys-Gly-Lys, -Cys-Lys-Lys, -Cys-Lys-Gly, -Cys-Gly-Arg, -Cys-Arg-Arg, and -Cys-Arg-Gly; dipeptide-mercapto-acylate such as -Asp-Asp-mercaptoacetyl, -Gly-Asp-mercaptoacetyl, and -Gly-Gly-mercaptoacetyl; a nitrogen-containing cyclic compound having 8 to 20 carbon atoms such as 1,4,7,10-tetraazacyclododecane (Cyclen), 1,4,8,11-tetraazacyclotetradecane (Cyclam), 1,4,8,12-tetraazacyclopentadecane, and 1,4,8,11-tetraazacyclotetradecane-5,7-dione (Dioxocyclam); a nitrogen-containing cyclic carboxylic acid compound having 8 to 20 carbon atoms such as 1,4,8,11-tetraazacyclotetradecane-1,4,8,11-tetraacetic acid (TETA), 1,4,7,10-tetraazacyclododecane-N,N',N'',N'''-tetraacetic acid (DOTA), 1,4,8,11-tetraazacyclotetradecane-5,7-dione-N,N',N'',N'''-tetraacetic acid, 1,4,7,10-tetraazacyclododecane-butyric acid, and 1,4,8,10-tetraazacyclododecane-butyric acid; a derivative of a nitrogen-containing cyclic carboxylic acid compound having 8 to 20 carbon atoms such as 1,4,7,10-tetraazacyclododecane-1-aminoethylcarbamoylmethyl-4,7,10-tris(R,S)-methylacetic acid (DO3MA), and 1,4,7,10-tetraazacyclododecane-1,4,7,10-α,α',α'',α'''-tetramethylacetic acid (DOTMA); and alkylene-amine-carboxylic acid having 4 to 10 carbon atoms such as ethylenediaminetetraacetic acid (EDTA), diethylenetriaminepentaacetic acid (DTPA), triethylenetetraminehexaacetic acid, and ethylene glycol-(2-aminoethyl)-N,N,N',N'-tetraacetic acid (EGTA).

The specific compound represented by chemical formula (1) is preferably a compound wherein in the formula (1), Z represents a formyl group. Examples thereof include
N-formyl-Nle-Leu-Phe-Nle-Tyr-Lys($NH_2$)-ε(-Ser-Cys-Gly-Asn) (SEQ ID NO:1),
N-formyl-Nle-Leu-Phe-Nle-Tyr-Lys($NH_2$)-ε(-Ser-Cys-Gly-Asp) (SEQ ID NO:2),
N-formyl-Nle-Leu-Phe-Nle-Tyr-Lys-ε(-Ser-Cys-Asp-Asp) (SEQ ID NO:3),
N-formyl-Nle-Leu-Phe-Nle-Tyr-Lys($NH_2$)-ε(-Ser-D-Arg-Asp-Cys-Asp-Asp) (SEQ ID NO:4),
N-formyl-Nle-Leu-Phe-Nle-Tyr-Lys($NH_2$)-ε(-Ser-D-Arg-diethylenetriaminepentaacetic acid (DTPA)) (SEQ ID NO:5),
N-formyl-Nle-Leu-Phe-Nle-Tyr-Lys($NH_2$)-ε(-Ser-diethylenetriaminepentaacetic acid (DTPA)) (SEQ ID NO:6),
N-formyl-Met-Leu-Phe-Lys-ε(-Asp-Asp-mercaptoacetyl) (SEQ ID NO:7),
N-formyl-Met-Leu-Phe-Lys-ε(-Gly-Asp-mercaptoacetyl) (SEQ ID NO:8),
N-formyl-Met-Leu-Phe-Lys-ε(-Gly-Gly-mercaptoacetyl) (SEQ ID NO:9),
N-formyl-Met-Leu-Phe-Lys-ε(-Asp-Gly-mercaptoacetyl) (SEQ ID NO:10),
N-formyl-Met-Leu-Phe-Lys-ε(diethylenetriaminepentaacetic acid (DTPA)) (SEQ ID NO:11), and
N-formyl-Met-Leu-Phe-Lys-hydrazinonicotinic acid (SEQ ID NO:12).

More preferable examples thereof include N-formyl-Nle-Leu-Phe-Nle-Tyr-Lys($NH_2$)-ε(-Ser-Cys-Gly-Asn) (SEQ ID NO:1),
N-formyl-Nle-Leu-Phe-Nle-Tyr-Lys($NH_2$)-ε(-Ser-Cys-Gly-Asp) (SEQ ID NO:2),
N-formyl-Nle-Leu-Phe-Nle-Tyr-Lys-ε(-Ser-Cys-Asp-Asp) (SEQ ID NO:3),
N-formyl-Nle-Leu-Phe-Nle-Tyr-Lys($NH_2$)-ε(-Ser-D-Arg-Asp-Cys-Asp-Asp) (SEQ ID NO:4),
N-formyl-Nle-Leu-Phe-Nle-Tyr-Lys($NH_2$)-ε(-Ser-D-Arg-diethylenetriaminepentaacetic acid (DTPA)) (SEQ ID NO:5),
N-formyl-Met-Leu-Phe-Lys-ε(-Asp-Asp-mercaptoacetyl) (SEQ ID NO:7),
N-formyl-Met-Leu-Phe-Lys-ε(-Gly-Asp-mercaptoacetyl) (SEQ ID NO:8), and
N-formyl-Met-Leu-Phe-Lys-ε(-Gly-Gly-mercaptoacetyl) (SEQ ID NO:9).

When the compound represented by chemical formula (1) is used in the present invention, a compound in which the group capable of being labeled with a metal is protected with an appropriate protecting group can also be used.

The above-described peptide capable of being labeled with a metal such as the leukocyte-binding compound can be synthesized by a method described below.

(1) A peptide consisting of amino acids can be synthesized by a Boc method or Fmoc method or the like using a generally used automatic peptide synthesizer such as automatic peptide synthesizers manufactured by Applied Biosystems. The synthesized complex, which is bound with a resin carrier for a solid phase, is simultaneously subjected to the removal of the protecting group and the separation thereof from the resin carrier and can be purified by high-performance liquid chromatography (hereinafter, referred to as HPLC) using a reverse-phase column or the like. Alternatively, the peptide may be prepared by liquid-phase peptide synthesis or may be collected from animals and so on.

(2) A peptide which contains a non-amino acid compound can be synthesized by the same method as above in most cases. For example, a Lys residue or protected derivative thereof is bonded to a resin carrier in a solid phase. To the N terminus thereof, an amino acid residue or protected derivative thereof or a compound or protected derivative thereof with a function as a spacer represented by X, a Phe residue or protected derivative thereof, a Leu residue or protected derivative thereof, and an amino acid or protected derivative thereof represented by Y are sequentially bonded thereto. Subsequently, the ε-amino group, a side chain of Lys bound with the resin carrier for a solid phase, is activated and bonded to Ser or Thr or protected derivative thereof represented by R and then to an amino acid or protected derivative thereof as a spacer or a compound or protected derivative thereof with a function as a spacer represented by T, and to a compound or protected derivative thereof capable of serving as the group capable of being labeled with a metal represented by U. The synthesized product of interest represented by the above-described formula (1) can be separated from the resin carrier to synthesize the peptide.

Other peptides capable of being labeled with a metal can be synthesized easily by adopting the above-described methods.

The amount of usage of the peptide capable of being labeled with a metal in the medical composition of the present invention can generally be in the range preferable for diagnosis and treatment of interest. This range is preferably a range acceptable in terms of safety. When a peptide that acts on a receptor is used, it is preferred that the peptide should be used in an amount equal to or smaller than that of the receptor of interest. To be more specific, the amount of usage of the peptide is preferably in the concentration range of 0.1 nM to 10 µM.

The medical composition of the present invention is prepared by dissolving the above-described peptide capable of being labeled with a metal together with the basic organic compound in an aqueous solvent, specifically in a solvent of sterile water, if necessary supplemented with other organic solvents. A desired additive can further be added thereto, if necessary. Examples of the additive can include a surfactant, hydrophilic organic solvent, reductant, pH adjuster, and stabilizer.

Examples of the surfactant can include, but not particularly limited to, nonionic surfactants such as polyoxyethylene sorbitan monolaurate, polyoxyethylene sorbitan monopalmitate, polyoxyethylene sorbitan monostearate, polyoxyethylene sorbitan tristearate, polyoxyethylene sorbitan monooleate, polyoxyethylene sorbitan trioleate, polyethylene glycol 200, polyethylene glycol 300, polyethylene glycol 600, polyethylene glycol 1000, and polyethylene glycol 1540. Preferably, polyoxyethylene sorbitan monooleate is used. The amount of the surfactant added is preferably 0.01 to 1% by weight, more preferably 0.05 to 0.5% by weight, in the medical composition.

Examples of the hydrophilic organic solvent may include, but not particularly limited to, polar organic solvents such as ethanol, propanol, butanol, acetonitrile, acetone, and methylethylketone. The amount of the hydrophilic organic solvent added is preferably 0.1 to 10% by weight, more preferably 0.2 to 1% by weight, in the medical composition.

The reductant is added for preventing the oxidation of the labeled metal. Examples of the reductant can include, but not particularly limited to, stannous chloride, ascorbic acid, and sodium borohydride. The concentration of the reductant added is preferably in the range of 0.01 mM to 10 mM, more preferably 0.05 mM to 1 mM, in the medical composition.

Examples of the pH adjuster can include, but not particularly limited to, hydrochloric acid, acetic acid, trifluoroacetic acid (hereinafter, referred to as "TFA"), citric acid, phosphoric acid, ascorbic acid, sodium hydroxide, and ammonia.

Examples of the stabilizer can include, but not particularly limited to, ascorbic acid, sodium ascorbate, p-aminobenzoic acid, sodium p-aminobenzoate, gentisic acid, and sodium gentisate. The concentration of the stabilizer added is preferably in the range of 0.1 mM to 1 M, more preferably 5 mM to 500 mM, in the composition.

The medical composition according to the present invention can be used in the form of an aqueous solution in which the peptide capable of being labeled with a metal and the basic organic compound are dissolved in the aqueous solvent, or can be prepared into a freeze-dried form by freeze-drying the medical composition in the form of an aqueous solution. The freeze-dried medical composition is easily capable of being used in kits or diagnostic drugs or pharmaceutical drugs for therapeutic use in other forms and can be used easily as a final material for an injection. When the medical composition is freeze-dried, the medical composition that is used in the form of an aqueous solution in which the peptide capable of being labeled with a metal and the basic organic compound are dissolved in the aqueous solvent can be freeze-dried by a usual method.

The medical composition of the present invention in the form of an aqueous solution or in the freeze-dried form can be applied together with a labeling reagent containing a metal and so on to a diagnostic drug or a pharmaceutical drug for therapeutic use.

The peptide capable of being labeled with a metal in the medical composition of the present invention can be labeled efficiently with a metal. A medical preparation prepared by labeling the medical composition with a metal can be accumulated in inflammation sites with immune response by the action of the peptide and can image the above-described sites by the labeled metal, for example when a peptide such as a leukocyte-binding compound that can be utilized in the imaging of inflammation sites is used as the peptide capable of being labeled with a metal. To be more specific, the use of the medical preparation according to the present invention as a radioactive diagnostic agent and an MRI contrast agent allows for the imaging of the inflammation sites. The preparation of the present invention can be used not only in imaging but also as a radioactive therapeutic agent by selecting a proper radioactive metal.

When the preparation is used as a radioactive diagnostic agent, it is preferred that the metal-labeled peptide in the medical composition of the present invention should be a radioactive metal-labeled peptide that is labeled with a radioactive metal for SPECT such as Tc-99m, In-111, Ga-67, Sn-117m, Sm-153, and Re-186, or a radioactive metal for PET such as Cu-64 and Ga-68. When the preparation is used as an MRI contrast agent, it is preferred that the metal-labeled peptide should be a paramagnetic metal-labeled peptide in which a paramagnetic metal such as Cu, Fe, Mn, Gd, and Dy is coordinated to the above-described peptide. When the preparation is used as a radioactive therapeutic agent, it is preferred that the metal-labeled peptide should be a radioactive metal-labeled peptide in which the above-described peptide is labeled with a radioactive metal such as Y-90, Re-186, and Re-188.

A variety of methods can be used for labeling the above-described peptide with a metal, for example a radioactive metal or paramagnetic metal. For example, when the peptide is labeled with Tc-99m, Re-186, or Re-188, a labeled compound can be prepared by a routine method in which a stable amount of a reductant acceptable as a pharmaceutical additive such as stannous chloride is added to the medical composition of the present invention and then mixed with a sodium pertechnetate solution or sodium perrhenate solution. When the peptide is labeled with Cu, Cu-64, Fe, Mn, Gd, In-111, Sn-117m, Sm-153, or Dy, a labeled compound can be prepared by mixing the medical composition according to the present invention with a weakly acid, water-soluble solution containing Cu, Cu-64, Fe, Mn, Gd, In-111, Sn-117m, Sm-153, or Dy ions. In this case, it is preferred that the final pH should be adjusted to 8 or higher. When the peptide is labeled with Ga-67, Ga-68, or Y-90, the labeling may be performed by mixing the medical composition according to the present invention with a weakly acid or alkaline, water-soluble solution containing Ga-67, Ga-68, or Y-90 ions. In this case, it is preferred that the final pH should be adjusted to 8 or higher.

The peptide may be labeled with a metal at room temperature for 5 minutes to 24 hours, preferably 5 to 60 minutes, more preferably 10 to 30 minutes, with stirring, shaking, or the like.

The medical preparation comprising the radioactive metal- or paramagnetic metal-labeled peptide is further supplemented with a pharmacologically acceptable additive, if necessary, and can be prepared into a preferable radioactive diagnostic agent or radioactive therapeutic agent. Examples of the additive include: a stabilizer such as pharmacologically acceptable ascorbic acid, sodium ascorbate, p-aminobenzoic acid, sodium p-aminobenzoate, gentisic acid, and sodium gentisate; a pH adjuster such as aqueous buffer solutions; an excipient such as D-mannitol; and citric acid, tartaric acid, malonic acid, sodium gluconate, and sodium glucoheptonate, which are useful for improving radiochemical purities.

When the medical preparation of the present invention comprising the radioactive metal- or paramagnetic metal-labeled peptide is used as a radioactive diagnostic agent, radioactive therapeutic agent, or MRI contrast agent, the preparation can be administered by generally used parenteral means such as intravenous administration. The dose thereof is determined in consideration of conditions such as the body weight and age of a patient, an appropriate radiographic imaging apparatus or MRI measuring apparatus, and symptoms of target disease.

For example, when a human is targeted, the dose of a diagnostic agent using the Tc-99m-labeled peptide is in the range of 37 MBq to 1110 MBq, preferably 185 MBq to 1110 MBq. The dose of a therapeutic agent using the Re-186- or Re-188-labeled peptide is in the range of 37 MBq to 18500 MBq, preferably 370 MBq to 7400 MBq. The dose of a therapeutic agent using the Y-90-labeled peptide is in the range of 37 MBq to 3700 MBq, preferably 37 MBq to 1110 MBq. The doses of agents using the labeled peptides that are labeled with other radioactive metals are almost the same as above. The dose of a therapeutic agent using the labeled peptide that is labeled with a paramagnetic metal such as Gd, Fe, Mn, Cu, and Dy is appropriately selected according to the sensitivity of an MRI imaging apparatus, a target tissue, a particular administration style, and the intended effect of usage.

For example, when the preparation using Gd as the metal is intravenously administered to a human, the dose thereof that is preferably used is usually 0.01 to 0.3 mmol/kg of body weight.

Hereinafter, the present invention will be described more fully with reference to Examples of the present invention. However, the present invention is not limited to these Examples by any means.

A method for measuring substances obtained in Examples, reagents used, etc will be shown below.

(1) Gamma counter: distribution in blood was measured with an Auto Well Gamma Counter (manufactured by Aloka). In in-vivo distribution studies, measurement was performed with NaI Single-Channel Analyzer (manufactured by Ohyo Koken Kogyo).

(2) Gamma camera: measurement was performed with GMS-550U (manufactured by Toshiba medical) or Millennium MG (manufactured by GE Yokogawa Medical Systems).

(3) Reverse-phase HPLC: a reverse-phase column Cosmosil $5C_{18}$-AR-300 (manufactured by Nacalai Tesque, 4.6×150 mm) was used.

(4) All peptide compounds were produced by solid-phase synthesis.

(5) Those eluted in a physiological saline by use of a $^{99m}TcO_4-$: $^{99}Mo/^{99m}Tc$ generator (trade name: Meditech, manufactured by Nihon Medi-Physics) were used.

(6) All reagents used were special grade or higher grade products.

(7) All experimental animals were raised for 1 week under conditions of a cycle of 12-hour light and 12-hour dark prior to experiments. During this period, they freely consumed foods and water.

(8) Peptides used in the present Examples were peptides described below.

Peptide 1: formyl-Nle-Leu-Phe-Nle-Tyr-Lys(NH$_2$)-ϵ(-Ser-D-Arg-Asp-Cys-Asp-Asp) (SEQ ID NO:4)

Peptide 2: formyl-Nle-Leu-Phe-Nle-Tyr-Lys(NH$_2$)-ϵ(-Ser-D-Arg-DTPA*) (SEQ ID NO:5)

Peptide 3: formyl-Met-Leu-Phe-Lys-ϵ(-Gly-Asp-Ac—S-Bzl) (SEQ ID NO:8)

*: DTPA: diethylenetriaminepentaacetic acid.

(9) Synthesis of Peptide 1

Peptide 1 was produced by solid-phase synthesis and used in Examples described below.

A peptide synthesizer (model: 430A) manufactured by Applied Biosystems was used to synthesize a peptide by a Boc method using an MBHA resin (p-Methoxy-Benzhydrylamine Resin hydrochloride, 1% Divinylbenzene-polystyrene copolymer) under conditions of 0.5 mM scales. In this procedure, the C terminus and the side chain of the Lys residue were protected with Fmoc groups. The peptide chain was elongated, and the N-terminal amino group was formylated. The Fmoc group of the side chain of the Lys residue was cleaved with 20% piperidine/DMF, and the peptide chain was elongated in the direction of the side chain. The peptide was separated therefrom through its reaction at −2° C. to −5° C. for 1.0 hour in anhydrous hydrogen fluoride:p-cresol (80:20).

Main peaks of the synthesized peptide were fractionated by HPLC (Column: YMC-Pack ODS-A SH-365-5 (trade name, manufactured by YMC, 30×250 mm), Column temperature: room temperature, Elution rate: 20 mL/min, Detector: ultraviolet and visible spectrophotometer (absorption wavelength: 220 nm), Eluant A: 0.1% TFA/purified water, Eluant B: 0.1% TFA/acetonitrile (A/B (80%/20%)→A/B (30%/70%), 90 min)), followed by freeze drying. The obtained peptide was analyzed by reverse-phase HPLC (Column: Zorbax 300SB-C18 (trade name, manufactured by Yokogawa Analytical Systems, 4.6×150 mm, Column temperature: 50° C., flow rate: 1.0 mL/min, Detector: ultraviolet and visible spectrophotometer (absorption wavelength: 220 nm), Eluant A: 0.1% TFA/purified water, Eluant B: 0.1% TFA/acetonitrile (A/B (80%/20%)→A/B (30%/70%), 25 min)). As a result, the purity of the obtained peptide was 93.2% (area percentage).

The peptide could also be synthesized by using a preloaded resin instead of the MBHA resin.

The above-described purified peptide was decomposed into each amino acid through its hydrolysis in 6 M hydrochloric acid at 110° C. for 22 hours. Amino acid composition was determined with L-8800-model Hitachi High-Speed Amino Acid Analyzer (trade name, manufactured by Hitachi High-Technologies) under conditions described below to confirm that the amino acids had the same amino acid composition as that of Peptide 1. Moreover, mass spectrometry (hereinafter, ESI-MS) was conducted to confirm that the results of the amino acids were identical to the theoretical value of Peptide 1.

Analytical Conditions for Amino Acid Composition

Model: L-8800-model Hitachi High-Speed Amino Acid Analyzer

Chromatography Conditions

Column size: 4.6 mm I.D.×60.0 mm

Stationary phase: Hitachi Custom Ion-Exchange Resin #2622

Mobile phase: Step-wise elution with sodium citrate buffer solutions (4 types, and for regeneration of analytical column, 0.2 N NaOH test solution)
  (1) L-8500-PH1: 0.16 N, pH 3.3
  (2) L-8500-PH2: 0.2 N, pH 3.2
  (3) L-8500-PH3: 0.2 N, pH 4.0
  (4) L-8500-PH4: 1.2 N, pH 4.9

Flow rate: 0.40 mL/min

Column temperature: 57° C.

Detection
  Reagent: (1) ninhydrin test solution, (2) buffer solution for ninhydrin (Ninhydrin Reagent L-8500 Set)

Flow rate of reaction reagent: 0.35 mL/min

Reaction apparatus: electron heating reaction column,

Temperature set: 135° C.

Detection wavelength: 570 nm and 440 nm

Standard Amino Acid

Reagent: Ajinomoto Amino Acid Calibration Mixture

Concentration: 50 nmol/mL each (however, 100 nmol/mL for Pro)

Diluent: 0.2 M Na Citrate Buffer (pH 2.2)

Injected amount: 40 μL (2 nmol each of amino acids and 4 nmol of Pro)

Calculation method for quantification: one-point absolute calibration curve method on the basis of area values The analysis value (the number of amino acids per molecule) of amino acid composition of the obtained Peptide 1 and a result of mass spectrometry thereof are shown below. Numerals in parentheses represent the theoretical values of amino acid composition of the peptide of interest.
  Peptide 1=Asp: (3) 3.19, Ser: (1) 0.97, Tyr: (1) 0.97, Phe: (1) 0.98, Lys: (1) 1.00, $NH_3$ (1) 1.20, Leu (1)+Nle (2) 2.80, Arg: (1) 1.06, Cys: (1) 0.92

The analysis value of ESI-MS of the obtained Peptide 1 is shown below. A numeral in a parenthesis represents the theoretical value of a molecular weight of the peptide of interest.
  ESI-MS: MW=514.4 (1514.7)

Example 1

Solubility of Peptide by Arginine (1) Procedures

Peptide 1, Peptide 2, and Peptide 3 (100 μg each) were separately added to 410 mM arginine solutions (pH 11) to adjust each total amount to 700 μL. Molarities in these solutions are 94 μM (Peptide 1), 99 μM (Peptide 2), and 161 μM (Peptide 3). The presence or absence of white turbidity was confirmed by external observation. Then, 200 μL each of the sample solutions was filtered with a filter Millex (registered trademark)-GV (trade name, manufactured by Nihon Millipore) with a pore size of 0.22 μm. The sample solutions before filtration and the sample solutions after filtration were respectively analyzed by reverse-phase HPLC. Peak area percentages were determined from the peak area values of the peptides before and after filtration and used as elution rates. HPLC analytical conditions are shown below.

For a comparative example, Peptide 1, Peptide 2, and Peptide 3 were separately dissolved in each of water and dimethylsulfoxide (DMSO) to prepare samples having a peptide concentration of 94 μM, 99 μM, or 161 μM, which were studied in the same way as above.

HPLC Conditions
  Column: Cosmosil $5C_{18}$-AR-300 (Manufactured by Nacalai Tesque, 4.6×150 mm)
  Elution rate: 1 mL/min
  Detection: ultraviolet and visible spectrophotometer (detection wavelength: 220 nm)
  HPLC system: Alliance (manufactured by Waters, Japan)
  Eluant A: 0.1% trifluoroacetic acid (hereinafter, TFA)/purified water
  Eluant B: 0.1% TFA/acetonitrile
  Concentration gradient: 0 min (Eluant B 20%)→25 min (Eluant B 70%)

(2) Result

The obtained result is shown in Table 1 and FIG. 1. As a result of external observation after each peptide dissolution, white turbidity was observed in 3 types of peptides dissolved in water, whereas all 3 types of peptides exhibited colorless, transparent appearances in their aqueous solutions of arginine. Similar appearances were exhibited in the sample solutions of DMSO. For elution rates obtained by reverse-phase HPLC, all of the respective sample solutions of arginine and DMSO exhibited approximately 100% elution rates. These results demonstrated that arginine enhances peptide solubility, as with DMSO.

TABLE 1

Result of external observation and elution rate of each sample solution

| Peptide | Solvent | | | | |
|---|---|---|---|---|---|
| | Appearance | | | Elution rate | |
| | Water | Arginine | DMSO | Arginine | DMSO |
| Peptide 1 | Whitish | Colorless, transparent | Colorless, transparent | 100.8% | 98.6% |
| Peptide 2 | Whitish | Colorless, transparent | Colorless, transparent | 102.8% | 100.9% |
| Peptide 3 | Whitish | Colorless, transparent | Colorless, transparent | 101.3% | 108.5% |

Example 2

Solubility of Peptide 1 by Arginine, Lysine, and Histidine at each pH (1) Procedures Arginine, lysine, and histidine were separately dissolved in water to prepare 410 mM arginine solution, 489 mM lysine solution, and 90 mM histidine solution. An aqueous solution of sodium hydroxide and hydrochloric acid were added to these solutions to adjust the pH of the aqueous solutions of lysine and histidine to 8, 9, 10, and 11, and the pH of the aqueous solution of arginine to 8, 8.5, 9, 9.5, 10, and 11. Subsequently, Peptide 1 was added to these aqueous solutions to prepare 94 μM Peptide 1 solutions. The presence or absence of white turbidity was confirmed by external observation. Then, 200 μL each of the sample solutions was filtered with a filter Millex (registered trademark)-GV (trade name, manufactured by Nihon Millipore) with a pore size of 0.22 μm. The sample solutions before filtration and the sample solutions after filtration were respectively analyzed by reverse-phase HPLC. Peak area percentages were determined from the peak area values of Peptide 1 before and after filtration and used as elution rates. HPLC analytical conditions were the same as the conditions described in Example 1.

(2) Result

The obtained result is shown in Table 2. Evident white turbidity was observed in the aqueous solution of arginine at pH 8. Weak white turbidity was observed in the respective aqueous solutions of arginine, lysine, and histidine at pH 8.5 or less, whereas elution rates slightly more than 20% were observed in the aqueous solutions of lysine and histidine even at pH 8. These results demonstrated that lysine and histidine have peptide-dissolving effect even at pH 8. The aqueous solutions of arginine, lysine, and histidine became colorless, transparent solutions at pH 9 or more, and the elution rates of the peptide were 85% or more. Thus, these basic amino acids were shown to be capable of producing peptide solubility at pH 8 or more.

TABLE 2

Solubility of peptide 1 by arginine, lysine, and hystidine at each pH

|  | pH 8 | pH 8.5 | pH 9 | pH 9.5 | pH 10 | pH 11 |
|---|---|---|---|---|---|---|
| Arginine | Not measured (*) | 43.8% | 93.8% | 95.4% | 98.8% | 100.8% |
| Lysine | 21.0% | — | 89.0% | — | 83.6% | 85.9% |
| Histidine | 26.8% | — | 85.9% | — | 90.7% | 96.7% |

*Not measured by HPLC due to evident white turbidity confirmed in external observation Example 3

Solubility of Peptide 1 by Imidazole at each pH (1) Procedures

Imidazole was dissolved in water to prepare 1 mM imidazole solution. pH was adjusted to 8, 8.5, and 9 by adding an appropriate amount of hydrochloric acid to this solution. Subsequently, Peptide 1 was added to these imidazole solutions to prepare 94 μM Peptide 1 solutions. The presence or absence of white turbidity was confirmed by external observation. Then, 200 μL each of the sample solutions was filtered with a filter Millex (registered trademark)-GV (trade name, manufactured by Nihon Millipore) with a pore size of 0.22 μm. The sample solutions before filtration and the sample solutions after filtration were respectively analyzed by reverse-phase HPLC. Peak area percentages were determined from the peak area values of Peptide 1 before and after filtration and used as elution rates. HPLC analytical conditions were the same as the conditions described in Example 1.

(2) Result

The obtained result is shown in Table 3. All the solutions with pH 8, 8.5, and 9 were colorless and transparent and exhibited 80% or more elution rates at pH 8.5 and 9 or more. These results demonstrated that imidazole imparts high solubility to Peptide 1.

TABLE 3

Result of external observation and elution rate of Peptide 1 by imidazole at each pH

|  | Appearance | Elution rate |
|---|---|---|
| pH 8 | colorless, transparent | 64.9% |
| pH 8.5 | colorless, transparent | 80.8% |
| pH 9 | colorless, transparent | 99.2% |

Example 4

Solubility of Peptide 1 by a Variety of Additives (1) Procedures

Disodium hydrogen phosphate, sodium dihydrogen citrate, sodium ascorbate, and imidazole were separately dissolved in water to prepare their respective aqueous solutions with pH 9 at concentrations described in Table 4. pH adjustment was performed with hydrochloric acid and an aqueous solution of sodium hydroxide. The above-described aqueous solutions were separately added to the weighed Peptide 1 to prepare 94 μM Peptide 1 solutions. The presence or absence of white turbidity was confirmed by external observation. Similarly, the presence or absence of white turbidity was confirmed for the aqueous solutions of Peptide 1 dissolved in the aqueous solutions of arginine, lysine, and histidine, which were obtained in Example 2. These Peptide 1 solutions were compared with the Peptide 1 sample solutions using the respective aqueous solutions of disodium hydrogen phosphate, sodium dihydrogen citrate, and sodium ascorbate used as comparative controls. Subsequently, 200 μL each of the sample solutions was filtered with a filter Millex (registered trademark)-GV (trade name, manufactured by Nihon Millipore) with a pore size of 0.22 μm. The sample solutions before filtration and the sample solutions after filtration were respectively analyzed by reverse-phase HPLC. Peak area percentages were determined from the peak area values of Peptide 1 before and after filtration and used as elution rates. pH was measured after HPLC measurement and used as actually measured pH values. HPLC analytical conditions were the same as the conditions described in Example 1.

TABLE 4

Concentration in sample solution of each additive

| Solvent | Additive | Morality | Weight concentration | pH |
|---|---|---|---|---|
| Water | Arginine | 410 mM | 71.4 mg/mL | 9 |
|  | Histidine | 90 mM | 14 mg/mL | 9 |
|  | Lysine | 489 mM | 50 mg/mL | 9 |
|  | Disodium hydrogen phosphate | 100 mM | 14 mg/mL | 9 |
|  | Sodium ascorbate | 401 mM | 71.4 mg/mL | 9 |
|  | Sodium dihydrogen citrate | 243 mM | 71.4 mg/mL | 9 |
|  | Imidazole | 1 mM | 0.07 mg/mL | 9 |

(2) Result

Figure 2:
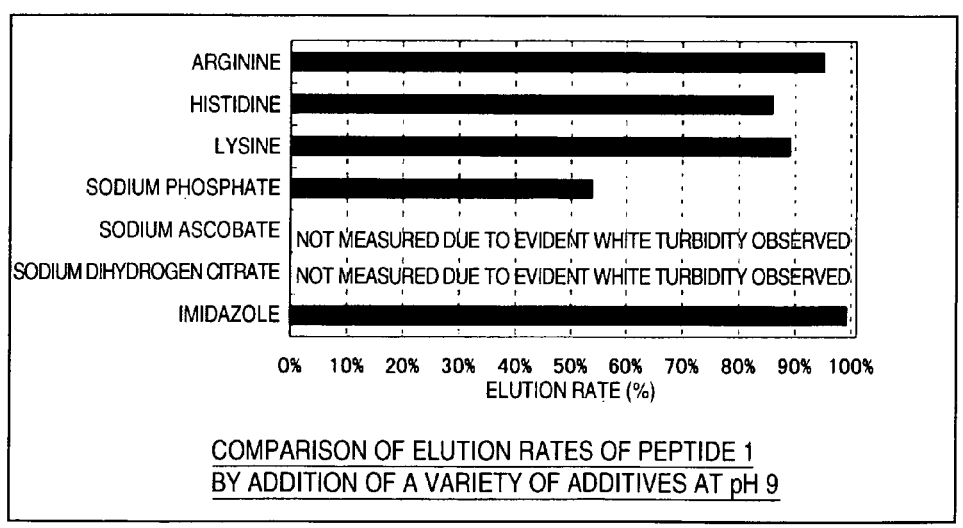
FIG. 2 is a diagram showing the comparison of the elution rates of Peptide 1 by the addition of a variety of additives at pH 9.

The obtained result is shown in Table 5 and FIG. 2. As a result of dissolution of Peptide 1, the aqueous solutions of 3 types of basic amino acids, arginine, lysine, and histidine, at pH 9 exhibited colorless, transparent appearances. The Peptide 1 sample solution using the aqueous solution of imidazole also exhibited a colorless, transparent appearance.

On the other hand, the respective aqueous solutions of sodium ascorbate and sodium dihydrogen citrate used as comparative controls exhibited white turbidity after the addition of Peptide 1. Although the aqueous solution of disodium hydrogen phosphate exhibited a colorless, transparent appearance after the addition of Peptide 1, its elution rate calculated by HPLC analysis exhibited a value of 53.8% and was low as compared with those of 3 types of basic amino acids and imidazole. These results demonstrated that these 3 types of basic amino acids and imidazole have not only solubility-promoting action by pH but also the action of enhancing the solubility of Peptide 1.

TABLE 5

Appearances, elution rate, and actually measured pH values of Peptide 1 solutions using a variety of aqueous solutions

| Solvent | Additive | pH | Elution rate | pH after preparation | Appearance |
|---|---|---|---|---|---|
| Water | Arginine | 9 | 93.8% | 8.97 | Colorless, transparent |
|  | Histidine | 9 | 85.9% | 9.00 | Colorless, transparent |
|  | Lysine | 9 | 89.0% | 8.99 | Colorless, transparent |
|  | Disodium hydrogen phosphate | 9 | 53.8% | 8.85 | Colorless, transparent |
|  | Sodium ascorbate | 9 | Not measured (*) | 9.10 | Whitish |
|  | Sodium dihydrogen citrate | 9 | Not measured | 9.05 | Whitish |
|  | Imidazole | 9 | 99.2% | 9.10 | Colorless, transparent |

*Not measured by HPLC due to evident white turbidity confirmed in external observation Example 5

Tc99m Labeling-Promoting Effect by Arginine (1) Procedures

Peptide 1 was dissolved in the aqueous solution of arginine with pH 10 obtained in Example 2 to prepare 9.4 μM peptide/arginine solution. 25 μL of a solution of 10 mL of 0.01 M hydrochloric acid supplemented with 5 mg of stannous chloride solution was added to 700 μL of the peptide/arginine solution, and 0.6 to 1.0 GBq of Tc-99m-sodium pertechnetate (hereinafter, 99 mTcO$_4^-$) solution was quickly added thereto to adjust the total amount to 1 mL. After the labeling procedure, the peptide concentration was diluted to 6.6 μM. After shaking for several seconds, the solution was reacted at room temperature. A portion thereof was taken on 10 minutes and 90 minutes after the labeling procedure to determine each Tc-99m labeling rate by HPLC and TLC. The HPLC and TLC analyses were performed under conditions described below.

For comparative controls, Peptide 1 was dissolved in dimethylsulfoxide (DMSO) and then diluted 10-fold with 100 mM phosphate buffer solution (hereinafter, PB) with pH 10 to prepare a peptide/DMSO/PB solution with the final peptide concentration of 9.4 μM. Alternatively, Peptide 1 was dissolved in PB to prepare a peptide/PB solution with the final peptide concentration of 9.4 μM. These solutions were labeled in the same way as in the peptide/arginine solution to determine each Tc-99m labeling rate by HPLC and TLC. After the labeling procedure, the peptide concentration was diluted to 6.6 μM.

HPLC Conditions
  Column: Cosmosil 5C$_{18}$-AR-300 (manufactured by Nacalai Tesque, 4.6×150 mm)
  Elution rate: 1 mL/min
  Detection: ultraviolet and visible spectrophotometer (detection wavelength: 220 nm)
  Radioactivity detector: STEFFI NaI scintillator (manufactured by Raytest)
  Eluant A: 0.1% TFA/purified water
  Eluant B: 0.1% TFA/acetonitrile
  Concentration gradient: 0 min (Eluant B 20%)→25 min (Eluant B 70%)

TLC conditions
  Plate: Silica Gel 60F254 (manufactured by Merck)
  Developing solvent: 28% ammonia water/acetonitrile=½
  Radioactivity detector: Gita NaI scintillator (manufactured by Raytest)

(2) Result

Radiochemical purities calculated from the resulting peak areas are shown in Table 6. The peptide solution using 410 mM arginine solution exhibited 90% or more radiochemical purity on 10 minutes after labeling and 95% or more radiochemical purity up to 90 minutes after labeling in HPLC analysis. Furthermore, it also exhibited 85% or more radiochemical purity on 10 minutes and 90 minutes after labeling in TLC analysis and was shown to have a high Tc99m labeling rate and high labeling stability without the need of heating.

On the other hand, radiochemical purities exhibited by the peptide/DMSO/PB solution and the peptide/PB solution used as comparative controls were 72.0% on 10 minutes after labeling and 75.4% on 90 minutes after labeling in HPLC analysis for the peptide/DMSO/PB solution, 45.7% on 10 minutes after labeling and 41.9% on 90 minutes after labeling in TLC analysis for the peptide/DMSO/PB solution, 55.3% on 10 minutes after labeling in HPLC analysis for the peptide/PB solution, and 28.0% on 10 minutes after labeling and 33.6% on 90 minutes after labeling in TLC analysis for the peptide/PB solution.

These results demonstrated that the peptide/arginine solution has a radiochemical purity higher than those of the comparative controls at both points in time. Accordingly, it was shown that the use of a dissolution method involving arginine addition can achieve a high labeling rate in a nonheated manner and improves the stability of the prepared labeled material.

TABLE 6

Radiochemical purity (%) in each solvent (pH 10) and temporal shifts thereof

|  | Arginine | | DMSO/phosphate buffer solution | | Phosphate buffer solution | |
|---|---|---|---|---|---|---|
|  | HPLC | TLC | HPLC | TLC | HPLC | TLC |
| 10 minutes | 92.5 | 87.2 | 72.0 | 45.7 | 55.3 | 28.0 |
| 90 minutes | 96.5 | 88.6 | 75.4 | 41.9 | — | 33.6 |

Example 6

Confirmation of Tc99m Labeling at Varying Arginine Concentrations and Stability Thereof (1) Procedures 12.5, 25, and 50 mg of arginine was weighed, then dissolved in water, and adjusted with hydrochloric acid to pH 10 to adjust each total amount to 700 μL. Molarities in these solutions are 102.5 mM, 205 mM, and 410 mM, respectively. Peptide 1 was dissolved in these aqueous solutions of arginine to prepare respective 9.4 μM peptide/arginine solutions. 25 μL of a solution of 10 mL of 0.01 M hydrochloric acid supplemented with 5 mg of stannous chloride solution was added to each of the peptide/arginine solutions, and 0.6 to 1.0 GBq of 99 mTcO$_4^-$ solution was quickly added thereto to adjust each total amount to 1 mL. After shaking for several seconds, the solutions were reacted at room temperature. A portion thereof was taken on 30 minutes, 90 minutes, 180 minutes, 360 minutes, 24 hours, and 30 hours after the labeling procedure to determine each radiochemical purity by TLC analysis under the conditions described in Example 5.

(2) Result

Radiochemical purities calculated from the peak areas are shown in Table 7. The peptide/arginine solutions exhibited 80% or more radiochemical purities in all the results up to 30 hours after labeling and further exhibited 85% or more radiochemical purities at arginine concentrations of 205 mM or less up to 30 hours after labeling. These results demonstrated that a dissolution method using arginine is capable of providing a Tc99m-labeled peptide exhibiting a high Tc99m labeling rate and high labeling stability without the need of heating in a manner independent of arginine concentrations.

TABLE 7

Radio chemical purity (%) at varying arginine concentrations and temporal shifts thereof

| | Radiochemical purity (%) at varying arginine concentrations | | |
|---|---|---|---|
| Elapsed time | 102.5 mM | 205 mM | 410 mM |
| 30 minutes | 93.3% | 92.0% | 91.6% |
| 90 minutes | 92.6% | 90.8% | 89.5% |
| 180 minutes | 92.6% | 89.7% | 87.1% |
| 360 minutes | 91.2% | 89.7% | 85.7% |
| 24 hours | 88.9% | 88.3% | 86.5% |
| 30 hours | 89.8% | 87.3% | 84.9% |

Example 7

Imaging of Rabbit Model of Infectious Disease Injected of Tc99m-Peptide 1 Solution Prepared by Arginine Addition in Rabbit Model of Infectious Disease (1) Procedures Approximately $10^8$ viable cells of *Staphylococcus aureus* were suspended in 1 mL of physiological saline. A 100-μL aliquot thereof was intramuscularly administered to the right thigh of each rabbit (New Zealand White, male, body weight of approximately 2 kg). After a lapse of 24 hours, the rabbit model in which inflammation was evidently observed was treated with pentobarbital anesthesia, and 37 to 74 MBq of the Tc99m-labeled Peptide 1 (arginine/nonheated) obtained in Example 5 was intravenously administered to the ear to take images with a gamma camera on 5 minutes, 1 hour, 2 hours, 3 hours, 4 hours, and 5 hours after administration. For a comparative control, Tc99m-labeled Peptide 1 (DMF/heated) prepared with peptide/dimethylformamide (DMF)/water and then heated was administered and studied in the same way.

Procedures for preparing the comparative control are as follows: 1.1 to 3.0 GBq of $^{99m}$TcO$_4^-$ solution was added into a vial containing a mixture solution of 300 μL of 134 mM glucoheptonic acid and 50 μL of 2.6 mM stannous chloride solution to adjust each total amount to 1.35 mL. The solutions were stirred by occasional inversion and reacted at room temperature for 30 minutes. A portion thereof was taken to confirm by cellulose acetate membrane electrophoresis that the Tc-99m labeling rate of Tc-99m-glucoheptonic acid was 95% or more. Next, Peptide 1 was dissolved in dimethylformamide (DMF) to prepare 943 μM Peptide 1 solution, which was in turn diluted 10-fold with water to prepare a 94 μM Peptide 1 solution. The Tc-99m-glucoheptonic acid solutions (300 μL each) were separately added to 700 μL of this solution, then mixed by stirring, and heated to 100° C. to 120° C. to react the solutions for 10 minutes. After labeling, a portion thereof was taken to determine each Tc-99m labeling rate by HPLC. HPLC conditions are as follows:

HPLC Conditions

Column: Puresil 5 μm C18 (manufactured by Millipore, 4.6×150 mm)

Elution rate: 1 mL/min

Detection: ultraviolet and visible spectrophotometer (detection wavelength: 220 nm)

Radioactivity detector: STEFFI NaI scintillator (manufactured by Raytest)

Eluant A: 0.1% TFA/purified water

Eluant B: 0.1% TFA/acetonitrile

Concentration gradient: 0 min (Eluant B 20%)→25 min (Eluant B 70%)

(2) Result

Figure 3:
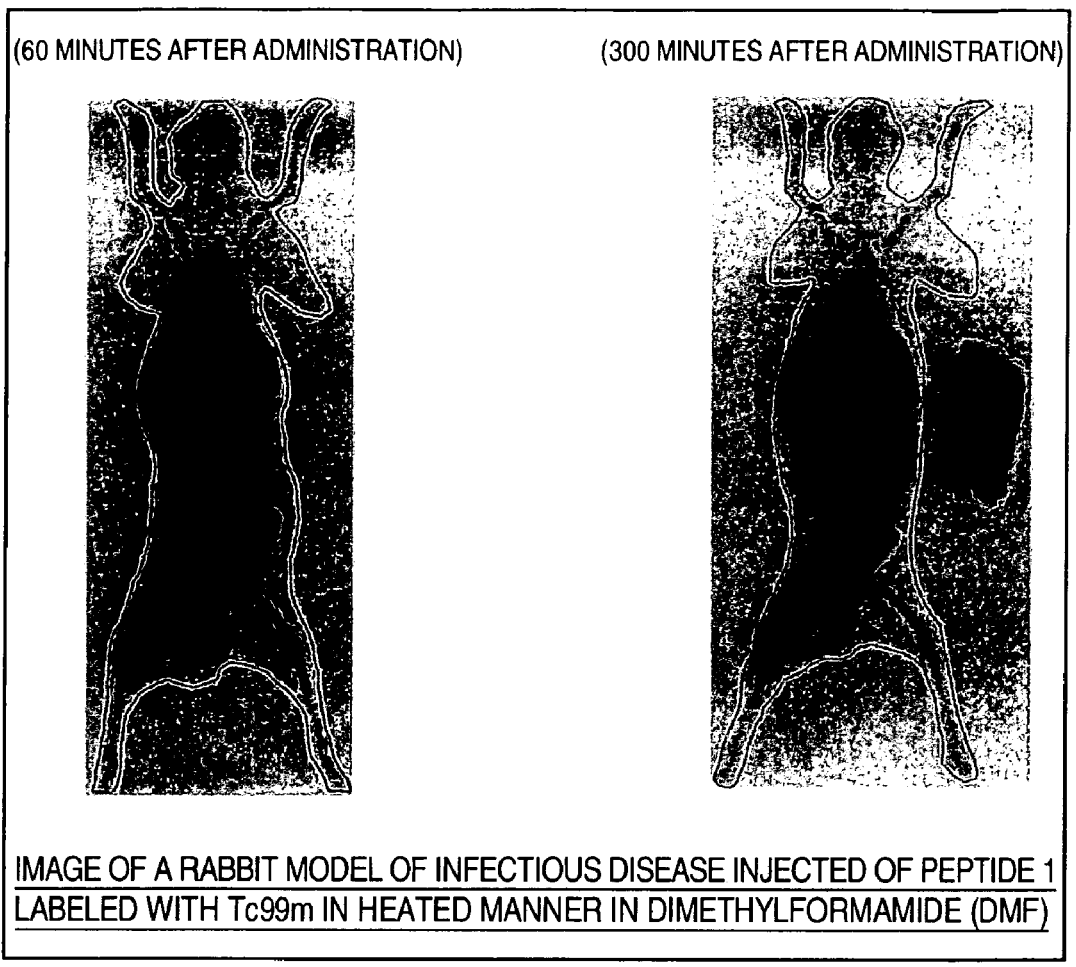
FIG. 3 is a diagram showing the image of a rabbit model of infectious disease injected of Peptide 1 labeled with Tc99m in a heated manner in dimethylformamide (DMF)
Figure 4:
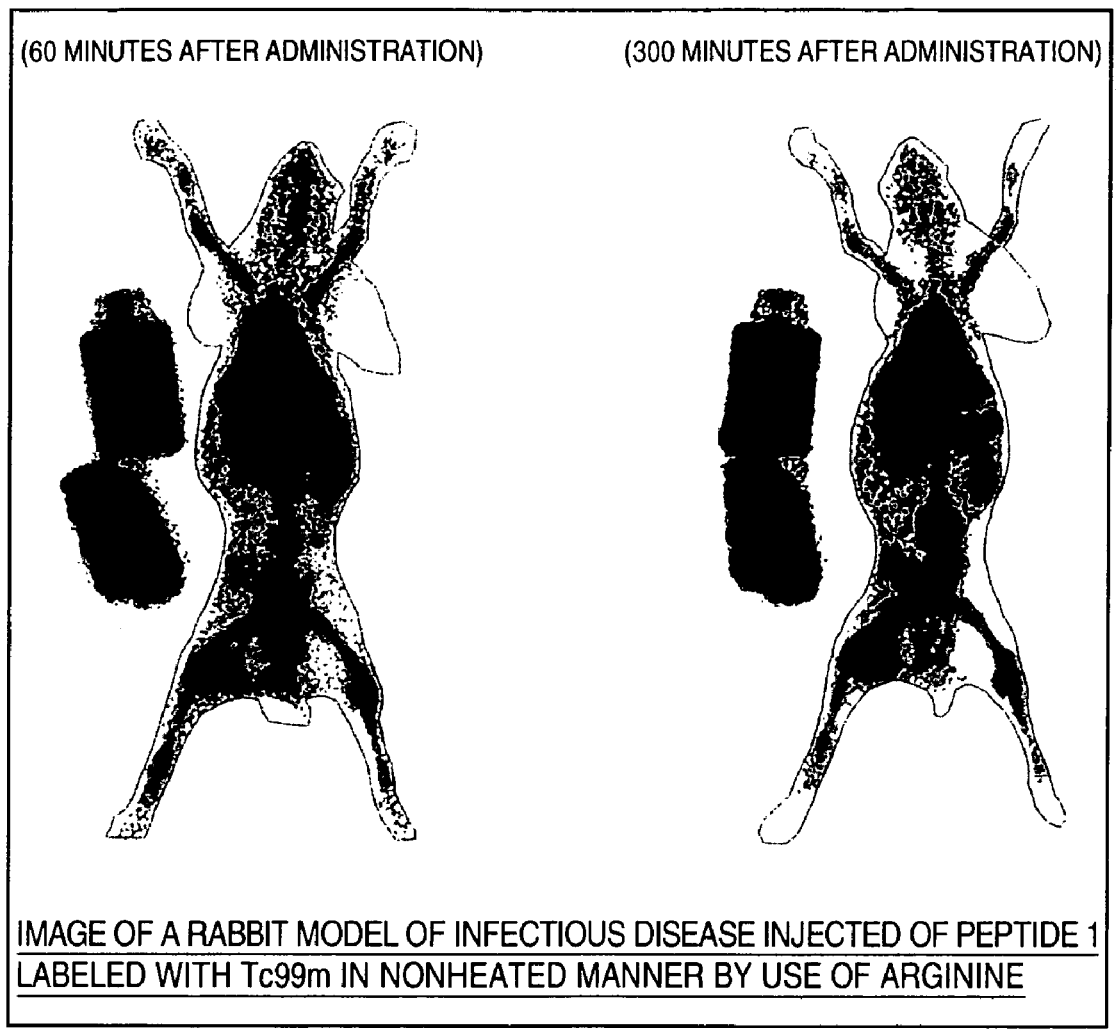
FIG. 4 is a diagram showing the image of a rabbit model of infectious disease injected of Peptide 1 labeled with Tc99m in a nonheated manner by use of arginine.
Figure 5:
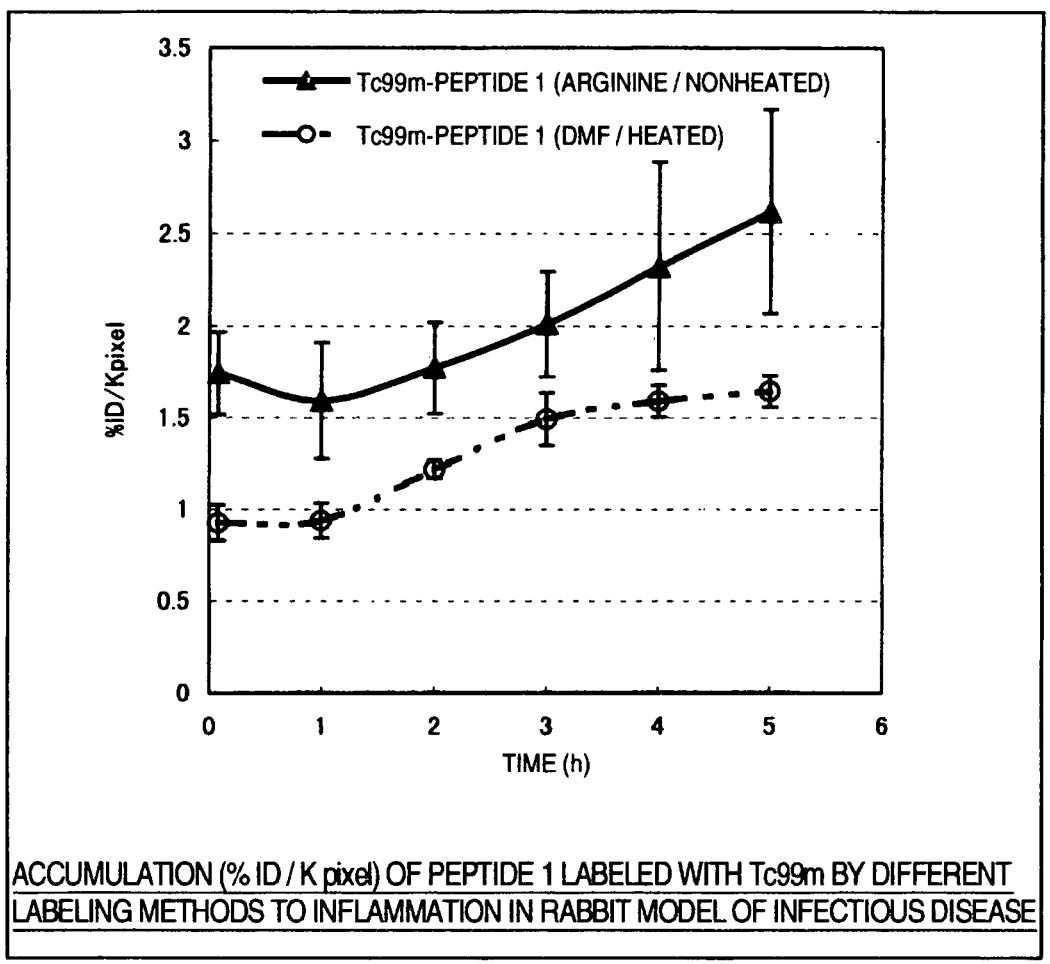
FIG. 5 is a diagram showing the accumulation (% ID/K pixel) of Peptides 1 labeled with Tc99m by different labeling methods to inflammation in a rabbit model of infectious disease.

Representative diagrams of the obtained results are shown in FIGS. 3 and 4. A result of setting a region of interest on the image to determine the proportion (% ID/K pixel) of a count per 1000 pixels of each region of interest with respect to the whole body count is shown in Table 8 and FIG. 5. As a result, infection sites could be visualized clearly in both the Tc99m-Peptide 1 (DMF/heated) of a conventional technique and the Tc99m-Peptide 1 (arginine/nonheated) of the present invention, and their visualized patterns were common to each other. The accumulation to inflammation of the formulation of the present invention, that is, the solution prepared by arginine addition under nonheated conditions exceeded that of the conventional method, that is, the solution prepared by DMF addition and heated to 100° C. or higher at all the points in time, and was increased from 1.59±0.32% ID/K pixel on 1 hour after administration to 2.62±0.55% ID/K pixel on 5 hours after administration. These results demonstrated that the method of the present invention in which a leukocyte-binding compound was dissolved in arginine and labeled with Tc99m in a nonheated manner can provide labeled materials having higher accumulation properties to inflammation than those of labeled materials obtained by conventional techniques.

TABLE 8

Accumulation (% ID/k pixel) of Peptides 1 labeled with Tc 99 m to inflammation in rabit model of infectious disease (N = 3, mean ± standard deviation)

| Labeling method | Elapsed time after administration | | | | | |
|---|---|---|---|---|---|---|
| | 5 minutes | 1 hour | 2 hours | 3 hours | 4 hours | 5 hours |
| Arginine/ nonheated | 1.74 ± 0.22 | 1.59 ± 0.32 | 1.77 ± 0.25 | 2.01 ± 0.29 | 2.32 ± 0.56 | 2.62 ± 0.55 |

TABLE 8-continued

Accumulation (% ID/k pixel) of Peptides 1 labeled with
Tc 99 m to inflammation in rabit model of infectious
disease (N = 3, mean ± standard deviation)

| Labeling | Elapsed time after administration | | | | | |
|---|---|---|---|---|---|---|
| DMF/heated | 0.95 ± 0.24 | 0.91 ± 0.14 | 1.09 ± 0.22 | 1.52 ± 0.27 | 1.76 ± 0.39 | 1.84 ± 0.27 |

INDUSTRIAL APPLICABILITY

The use of a medical composition according to the present invention improves the solubility of a peptide capable of being labeled with a metal, which is insoluble or poorly soluble in an aqueous solvent and allows for the metal-labeling of the above-described peptide without heating. The use of a metal-labeling method according to the present invention allows for the labeling of the above-described peptide with a metal under nonheated conditions. Furthermore, a preparation obtained by labeling, with a metal, the above-described peptide in the medical composition according to the present invention has the advantage of improving the accumulation rate of the peptide to inflammation as compared with that of a composition prepared by a conventional method, for example when the peptide that can be used in the imaging of inflammation is used therein. For example when a leukocyte-binding compound is used as the peptide, the present invention is capable of providing a medical composition and a medical preparation and a labeling method thereof being useful in PET diagnostic imaging, SPECT diagnostic imaging, and MRI diagnostic imaging that conduct the imaging of active leukocyte infiltration sites with the immune responses of individuals, or in radiation therapy.

The invention claimed is:

1. A medical composition, comprising:
a peptide labeled with a metal and
a basic organic compound acceptable as a pharmaceutical additive wherein the basic organic compound is a basic amino acid or a basic compound having an imidazole ring, wherein the peptide labeled with a metal is selected from the group consisting of N-formyl-Nle-Leu-Phe-Nle-Tyr-Lys(NH$_2$)-ϵ(-Ser-Cys-Gly-Asn) (SEQ ID NO:1), N-formyl-Nle-Leu-Phe-Nle-Tyr-Lys(NH$_2$)-ϵ(-Ser-Cys-Gly-Asp) (SEQ ID NO:2), N-formyl-Nle-Leu-Phe-Nle-Tyr-Lys-ϵ(-Ser-Cys-Asp-Asp) (SEQ ID NO:3), N-formyl-Nle-Leu-Phe-Nle-Tyr-Lys(NH$_2$)-ϵ(-Ser-D-Arg-Asp-Cys-Asp-Asp) (SEQ ID NO:4), N-formyl-Nle-Leu-Phe-Nle-Tyr-Lys(NH$_2$)-e(-Ser-D-Arg-diethylenetriaminepentaacetic acid (DTPA)) (SEQ ID NO:5), N-formyl-Met-Leu-Phe-Lys-ϵ(-Asp-Asp-mercaptoacetyl) (SEQ ID NO:7), N-formyl-Met-Leu-Phe-Lys-ϵ(-Gly-Asp-mercaptoacetyl) (SEQ ID NO:8), and N-formyl-Met-Leu-Phe-Lys-ϵ(-Gly-Gly-mercaptoacetyl) (SEQ ID NO:9).

2. The medical composition according to claim 1, wherein the basic amino acid is at least one selected from the group consisting of arginine, histidine, and lysine.

3. A diagnostic or therapeutic pharmaceutical comprising the medical composition of claim 1 and a pharmacologically acceptable additive.

4. The medical composition according to claim 1, wherein the peptide labeled with a metal is a peptide available as an active ingredient in a diagnostic drug or a pharmaceutical drug for therapeutic use.

5. The medical composition according to claim 1, wherein the composition further comprises one or more additives selected from a reductant, pH adjuster, surfactant, hydrophilic organic solvent, and stabilizer.

6. The composition of claim 1 in freeze-dried form.

7. The medical preparation according to claim 1 wherein the metal is a radioactive metal or paramagnetic metal.

8. The medical preparation according to claim 7, wherein the radioactive metal is selected from Tc-99m, In-111, Ga-67, Y-90, Sn-117m, Sm-153, Re-186, and Re-188.

9. The medical preparation according to claim 7, wherein the paramagnetic metal is selected from Gd, Fe, Mn, Cu, and Dy.

10. A method for labeling a peptide with a metal wherein the peptide is selected from the group consisting of N-formyl-Nle-Leu-Phe-Nle-Tyr-Lys(NH$_2$)-ϵ(-Ser-Cys-Gly-Asn) (SEQ ID NO: 1), N-formyl-Nle-Leu-Phe-Nle-Tyr-Lys(NH$_2$)-ϵ(-Ser-Cys-Gly-Asp) (SEQ ID NO: 2), N-formyl-Nle-Leu-Phe-Nle-Tyr-Lys-ϵ(-Ser-Cys-Asp-Asp) (SEQ ID NO: 3), N-formyl-Nle-Leu-Phe-Nle-Tyr-Lys(NH$_2$)-ϵ(-Ser-D-Arg-Asp-Cys-Asp-Asp) (SEQ ID NO: 4), N-formyl-Nle-Leu-Phe-Nle-Tyr-Lys(NH$_2$)-ϵ(-Ser-D-Arg-diethylenetriaminepenaacetic acid (DTPA)) (SEQ ID NO: 5), N-formyl-Met-Leu-Phe-Lys-ϵ(-Asp-Asp-mercaptoacetyl) (SEQ ID NO: 7), N-formyl-Met-Leu-Phe-Lys-ϵ(-Gly-Asp-mercaptoacetyl) (SEQ ID NO: 8), and N-formyl-Met-Leu-Phe-Lys-ϵ(-Gly-Gly-mercaptoacetyl) (SEQ ID NO: 9), comprising the steps of: dissolving the peptide in an aqueous solvent of a basic organic compound; and then labeling the resulting product with a metal.

11. The method according to claim 10, wherein the peptide labeled with a metal is insoluble or poorly soluble in an aqueous solvent.

12. The method according to claim 10, wherein the basic organic compound is a basic amino acid or a basic compound having an imidazole ring.

13. The method according to claim 12, wherein the basic amino acid is selected from the group consisting of arginine, histidine, and lysine.

14. The method according to claim 12, wherein the basic compound having an imidazole ring imidazole.

15. The method according to claim 10, wherein the metal is a radioactive metal or paramagnetic metal.

16. The method according to claim 15, wherein the radioactive metal is selected from Tc-99m, In-111, Ga-67, Y-90, Sn-117m, Sm-153, Re-186, and Re-188.

17. The method according to claim 15, wherein the paramagnetic metal is selected from Gd, Fe, Mn, Cu, and Dy.

* * * * *

SEQUENCE LISTING

```
<160> NUMBER OF SEQ ID NOS: 12

<210> SEQ ID NO 1
<211> LENGTH: 10
<212> TYPE: PRT
<213> ORGANISM: Artificial Sequence
<220> FEATURE:
<223> OTHER INFORMATION: chemically synthesized metal chelating peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (6)..(6)
<223> OTHER INFORMATION: AMIDATION

<400> SEQUENCE: 1

Leu Leu Phe Leu Tyr Lys Ser Cys Gly Asn
1               5                   10

<210> SEQ ID NO 2
<211> LENGTH: 10
<212> TYPE: PRT
<213> ORGANISM: Artificial Sequence
<220> FEATURE:
<223> OTHER INFORMATION: chemically synthesized metal chelating peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (6)..(6)
```

```
<223> OTHER INFORMATION: AMIDATION

<400> SEQUENCE: 2

Leu Leu Phe Leu Tyr Lys Ser Cys Gly Asp
1               5                   10

<210> SEQ ID NO 3
<211> LENGTH: 10
<212> TYPE: PRT
<213> ORGANISM: Artificial Sequence
<220> FEATURE:
<223> OTHER INFORMATION: chemically synthesized metal chelating peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (6)..(6)
<223> OTHER INFORMATION: AMIDATION

<400> SEQUENCE: 3

Leu Leu Phe Leu Tyr Lys Ser Cys Asp Asp
1               5                   10

<210> SEQ ID NO 4
<211> LENGTH: 12
<212> TYPE: PRT
<213> ORGANISM: Artificial Sequence
<220> FEATURE:
<223> OTHER INFORMATION: chemically synthesized metal chelating peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (6)..(6)
<223> OTHER INFORMATION: AMIDATION

<400> SEQUENCE: 4

Leu Leu Phe Leu Tyr Lys Ser Arg Asp Cys Asp Asp
1               5                   10

<210> SEQ ID NO 5
<211> LENGTH: 8
<212> TYPE: PRT
<213> ORGANISM: Artificial Sequence
<220> FEATURE:
<223> OTHER INFORMATION: chemically synthesized metal chelating peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (1)..(1)
```

```
<223> OTHER INFORMATION: FORMYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (6)..(6)
<223> OTHER INFORMATION: AMIDATION
<220> FEATURE:
<221> NAME/KEY: MOD_RES
<222> LOCATION: (8)..(8)
<223> OTHER INFORMATION: ACETYLATION

<400> SEQUENCE: 5

Leu Leu Phe Leu Tyr Lys Ser Arg
1               5

<210> SEQ ID NO 6
<211> LENGTH: 7
<212> TYPE: PRT
<213> ORGANISM: Artificial Sequence
<220> FEATURE:
<223> OTHER INFORMATION: chemically synthesized metal chelating peptide
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MOD_RES
<222> LOCATION: (4)..(4)
<223> OTHER INFORMATION: Nle
<220> FEATURE:
<221> NAME/KEY: MOD_RES
<222> LOCATION: (6)..(6)
<223> OTHER INFORMATION: AMIDATION
<220> FEATURE:
<221> NAME/KEY: MOD_RES
<222> LOCATION: (7)..(7)
<223> OTHER INFORMATION: ACETYLATION

<400> SEQUENCE: 6

Leu Leu Phe Leu Tyr Lys Ser
1               5

<210> SEQ ID NO 7
<211> LENGTH: 6
<212> TYPE: PRT
<213> ORGANISM: Artificial Sequence
<220> FEATURE:
<223> OTHER INFORMATION: chemically synthesized metal chelating peptide
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MOD_RES
<222> LOCATION: (4)..(4)
<223> OTHER INFORMATION: AMIDATION
<220> FEATURE:
<221> NAME/KEY: THIOLEST
<222> LOCATION: (6)..(6)

<400> SEQUENCE: 7

Met Leu Phe Lys Asp Asp
1               5

<210> SEQ ID NO 8
<211> LENGTH: 6
```

```
<212> TYPE: PRT
<213> ORGANISM: Artificial Sequence
<220> FEATURE:
<223> OTHER INFORMATION: chemically synthesized metal chelating peptide
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MOD_RES
<222> LOCATION: (4)..(4)
<223> OTHER INFORMATION: AMIDATION
<220> FEATURE:
<221> NAME/KEY: THIOLEST
<222> LOCATION: (6)..(6)

<400> SEQUENCE: 8

Met Leu Phe Lys Gly Asp
1               5

<210> SEQ ID NO 9
<211> LENGTH: 6
<212> TYPE: PRT
<213> ORGANISM: Artificial Sequence
<220> FEATURE:
<223> OTHER INFORMATION: chemically synthesized metal chelating peptide
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MOD_RES
<222> LOCATION: (4)..(4)
<223> OTHER INFORMATION: AMIDATION
<220> FEATURE:
<221> NAME/KEY: THIOLEST
<222> LOCATION: (6)..(6)

<400> SEQUENCE: 9

Met Leu Phe Lys Gly Gly
1               5

<210> SEQ ID NO 10
<211> LENGTH: 6
<212> TYPE: PRT
<213> ORGANISM: Artificial Sequence
<220> FEATURE:
<223> OTHER INFORMATION: chemically synthesized metal chelating peptide
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MOD_RES
<222> LOCATION: (4)..(4)
<223> OTHER INFORMATION: AMIDATION
<220> FEATURE:
<221> NAME/KEY: THIOLEST
<222> LOCATION: (6)..(6)

<400> SEQUENCE: 10

Met Leu Phe Lys Asp Gly
1               5

<210> SEQ ID NO 11
<211> LENGTH: 4
<212> TYPE: PRT
<213> ORGANISM: Artificial Sequence
<220> FEATURE:
<223> OTHER INFORMATION: chemically synthesized metal chelating peptide
<220> FEATURE:
<221> NAME/KEY: MOD_RES
<222> LOCATION: (1)..(1)
```

```
<223> OTHER INFORMATION: FORMYLATION
<220> FEATURE:
<221> NAME/KEY: MOD_RES
<222> LOCATION: (4)..(4)
<223> OTHER INFORMATION: ACETYLATION

<400> SEQUENCE: 11

Met Leu Phe Lys
1

<210> SEQ ID NO 12
<211> LENGTH: 4
<212> TYPE: PRT
<213> ORGANISM: Artificial Sequence
<220> FEATURE:
<223> OTHER INFORMATION: chemically synthesized metal chelating peptide
<220> FEATURE:
<221> NAME/KEY: MOD_RES
<222> LOCATION: (1)..(1)
<223> OTHER INFORMATION: FORMYLATION
<220> FEATURE:
<221> NAME/KEY: MOD_RES
<222> LOCATION: (4)..(4)
<223> OTHER INFORMATION: NICOTHYNATE

<400> SEQUENCE: 12

Met Leu Phe Lys
1
```